(12) United States Patent
Jacobsen et al.

(10) Patent No.: US 6,214,042 B1
(45) Date of Patent: Apr. 10, 2001

(54) MICRO-MACHINED STENT FOR VESSELS, BODY DUCTS AND THE LIKE

(75) Inventors: Stephen C. Jacobsen, Salt Lake City; John Lippert, Park City, both of UT (US)

(73) Assignee: Precision Vascular Systems, Inc., West Valley City, UT (US)

( * ) Notice: Subject to any disclaimer, the term of this patent is extended or adjusted under 35 U.S.C. 154(b) by 0 days.

(21) Appl. No.: 09/189,587

(22) Filed: Nov. 10, 1998

(51) Int. Cl.[7] ......................................................... A61F 2/00
(52) U.S. Cl. ............................................. 623/1.2; 623/1.22
(58) Field of Search ................................... 606/108, 198, 606/200; 424/429, 423; 623/1, 12, 11, 1.2–1.22

(56) References Cited

U.S. PATENT DOCUMENTS

| | | | |
|---|---|---|---|
| 4,994,069 | * | 2/1991 | Ritchart et al. ...................... 606/198 |
| 5,282,823 | * | 2/1994 | Schwartz et al. ..................... 606/198 |
| 5,437,288 | * | 8/1995 | Schwartz et al. ..................... 600/585 |
| 5,545,208 | * | 8/1996 | Wolf et al. ................................ 623/1 |
| 5,696,518 | * | 12/1997 | Laerum ................................ 606/198 |
| 5,707,389 | * | 1/1998 | Louw et al. ......................... 606/200 |
| 5,709,874 | * | 1/1998 | Hanson et al. ....................... 424/423 |
| 5,749,919 | * | 5/1998 | Blanc ................................. 623/1.22 |
| 5,797,953 | * | 8/1998 | Tekulve ............................... 606/200 |
| 5,814,063 | * | 9/1998 | Freitag ................................ 606/200 |
| 5,824,053 | * | 10/1998 | Khosravi et al. ........................ 623/1 |
| 5,851,232 | * | 12/1998 | Lois ........................................ 623/1 |
| 5,900,246 | * | 5/1999 | Lanbert ............................... 424/429 |

* cited by examiner

*Primary Examiner*—Michael J. Milano
(74) *Attorney, Agent, or Firm*—Thorpe North & Western, LLP

(57) ABSTRACT

A micromachined stent includes an elongate resilient wire formed into a coil for threading lengthwise into and through a catheter for ultimate discharge from the end of the catheter, to a target location in a blood vessel or body duct. When discharged, the wire resumes a coil form to hold the vessel or duct walls apart. Selective preferential flexibility is provided in the wire by placement of generally transversely formed cuts on the exterior of the wire.

16 Claims, 1 Drawing Sheet

MICRO-MACHINED STENT FOR VESSELS, BODY DUCTS AND THE LIKE

BACKGROUND OF THE INVENTION

This invention relates to devices for maintaining blood vessels or other body ducts in an open condition, and more particularly to a coil wire stent having selected flex/stiffness orientations.

Vascular medical treatment procedures are known to include, among other things, occluding a blood vessel by thrombogenic devices, and maintaining the blood vessels open by use of a stent. Stents typically used in the past have consisted of a stainless steel tube section which includes selectively positioned gaps or openings which enable the section to be expanded, for example, by a balloon catheter, after the section is positioned at the desired location in the blood vessel. The expansion of the tubular section may be likened in some aspect to the expansion of a molly bolt cartridge in which two ends are drawn together causing the center section to bow outwardly.

Problems with the above prior art stent, among other things, are that the length changes when the tubular section is expanded (the length shortened), and the length of the stent is limited since the longer is the length, the more difficult it is to deliver the stent to a target location in the blood vessel. That is, the stent, being rigid, does not navigate well in the blood vessel, especially around tight corners. Further, since the described stent cannot be very long, numerous stents must be used for a diffuse diseased blood vessel.

SUMMARY OF THE INVENTION

It is an object of the invention to provide a vasculature stent which is easily deployable in a vasculature or other body passageway to maintain the passageway in an open condition.

It is also an object of the invention to provide such a stent which is simple and inexpensive to manufacture.

It is a further object of the invention to provide such a stent which has stiffness/flexibility characteristics which accommodate the deployability of the stent and maintainability of the vasculature or other body passageway in the desired open condition.

The above and other objects are realized in a specific illustrative embodiment of a vasculature stent adapted for disposition in a blood vessel or other body duct to maintain the vessel or duct walls apart to allow the flow of blood or other duct function. This embodiment includes an elongate resilient wire or tube formed into a coil, which may be threaded lengthwise into and through a catheter for ultimate discharge therefrom to a target location in the blood vessel or duct. When the wire is discharged from the catheter, it resumes the coil form to thereby hold the vessel or duct walls apart.

In accordance with one aspect of the invention, the coil wire includes cuts selectively located on the exterior of the wire to provide flexibility in the direction of greatest curvature of the wire, and stiffness in the direction of least curvature of the wire. This enables the wire to be flexible for uncoiling the wire into an elongate shape for introduction into a catheter, while also allowing the wire to remain stiff in the transverse direction of the coil so that it is not easily compacted in that direction thereby serving to better maintain the vessel or duct patency.

In accordance with another aspect of the invention, the stent is formed from a hollow wire or tube, with cuts or openings formed to allow dispersion there through of medication carried in the hollow of the wire. With this configuration, a stent carrying medication or a therapeutic agent may be deposited in a vessel or duct so that the medication or agent flows from the stent to the vessel or duct walls to treat the problem—e.g. anti-restenosis agent, thrombolytic agent, etc.

BRIEF DESCRIPTION OF THE DRAWINGS

The above and other objects, features and advantages of the invention will become apparent from a consideration of the following detailed description presented in connection with the accompanying drawings in which.

DETAILED DESCRIPTION

Figure 1:
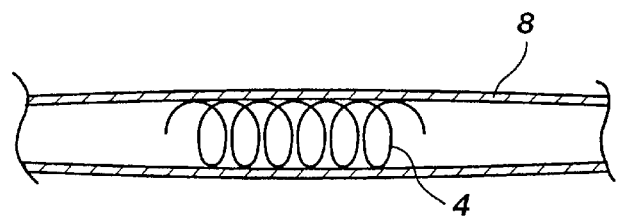
FIG. 1 is a side, cross-sectional view of a vascular/duct stent deployed in a blood vessel to maintain the blood vessel walls apart, in accordance with the principles of the present invention.
Figure 2:
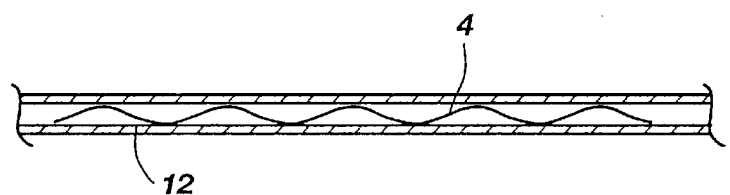
FIG. 2 is a side, cross-sectional view of the vascular/duct stent of FIG. 1 threaded lengthwise inside a catheter.

The stent of the present invention is formed of an elongate resilient wire or tube formed into a helical coil 4 (FIG. 1) which may be straightened and threaded or inserted lengthwise into and through a catheter 12 (FIG. 2) for ultimate discharge therefrom to a target location, for example, in a blood vessel 8 (FIG. 1). In other words, the wire stent 4 is formed to assume the shape of a helical coil when unconstrained, but is flexible enough to be pulled or extended into an elongate, straightened shape for threading lengthwise into and through the lumen of a catheter 12 as shown in FIG. 2. While the wire is constrained within the catheter, it is forced to retain the elongate, straightened shape. However, when the wire emerges from the end of the catheter so as to be unconstrained by the walls of the catheter, it resumes a helical coil form which functions as a stent.

The stent wire 4 may be tubular or solid and may, advantageously, be made of nickel-titanium alloy. In accordance with one aspect of the invention, the stent wire 4 is formed to provide preferential flexure/stiffness orientation which enables the coil to remain open and maintain the open profile of the vessel 8, i.e., to resist collapsing.

Figure 3A:
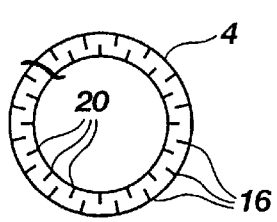
FIG. 3A is a fragmented, front view of the coil of FIG. 1, showing cuts formed in the stent to provide desired flexibility in the direction of greatest curvature of the stent.
Figure 3B:
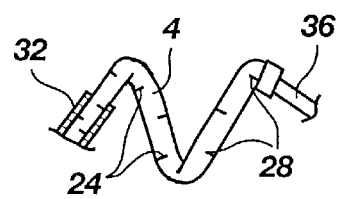
FIG. 3B is a fragmented, side view of the vascular/duct stent of FIG. 1, showing cuts formed in the stent to provide desired flexibility, but with greater stiffness, in the direction of least curvature of the stent.

FIGS. 3A and 3B show fragmented views, front and side, respectively of the wire 4 of FIG. 1. FIG. 3A shows cuts 16 and 20 formed generally transversely of the wire on the outside and inside respectively of the coils to provide greater flexibility in the direction of greatest curvature of the wire. This allows for easier navigation and delivery of the wire 4 through a catheter to target locations in blood vessels or other body ducts. Flexibility may be increased in one of a number of ways including making the cuts 16 and 20 deeper, providing more of such cuts, making such cuts wider, or a combination of these approaches. See, for example, co-pending U.S. patent application, Ser. No. 09/025,912, filed Feb. 19, 1998.

Once the coil stent 4 has been delivered through the catheter 12 to a target location in the blood vessel 8, the stent resumes the coil shape shown in FIG. 1 to spread and maintain apart the walls of the blood vessel. Of course, in this position, it is desired that the coil 4 be as resistant to collapsing as possible. To achieve this, cuts formed in the wire in the direction of least bending, i.e., on the forward and rearward sides of the wire, are either fewer in number, more shallow, less wide, or a combination of these. Such cuts 24 on the rearward side of the coil 4 and 28 on the forward side of the coil are shown in FIG. 3B. It is noted that the cuts 24 and 28 are shown to be fewer in number than cuts 16 and 20 of FIG. 3A as well as being more shallow. In this manner, some flexibility in the direction of least curvature of the wire achieved but greater stiffness and rigidity is maintained in this direction so that there is less likelihood that the coil, when deployed in a blood vessel, will collapse.

Figure 4:
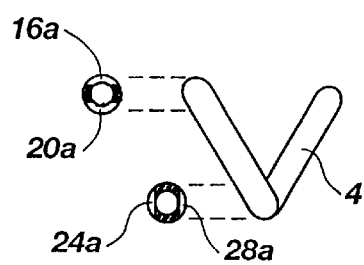
FIG. 4 shows a side view of a section of a stent illustrating the difference in depths of the cuts formed in a stent in one embodiment of the invention.

FIG. 4 depicts, schematically, cuts 16a and 20a formed in the outside and inside of the coil 4 to be deeper than cuts 24a and 28a formed on the rearward and forward sides respectively of the coil.

In the manner described, a stent is provided which is readily deployable into a blood vessel or other body duct and yet which is sufficiently rigid to maintain the blood vessel in an open condition. This is achieved by providing a selectively flexible coil which may be threaded lengthwise through a catheter to a target location in the blood vessel but when discharged from the catheter, the wire resumes its coil shape and is fairly stiff and rigid in a direction to prevent collapsing of the coil. The selective flexibility is achieved by the appropriate micromachining or placement of cuts in the coil wire.

An alternative embodiment to that described above involves employment of a hollow or tubular wire 4 to construct the stent, and provision of openings or cuts, such as those shown at 16 in FIG. 3A, preferably on the outside of the wire to allow medication or therapeutic agents carried in the hollow of the wire to flow thereout. The stent would be deployed in a blood vessel or duct in the manner described above, but with the stent carrying medication in the hollow of the wire 4. After deployment, the openings or cuts 16 on the outside of the wire would allow flow therethrough of medication carried by the wire. Advantageously, the openings or cuts would flex open further when the wire 4 resumed the coil shape (FIGS. 3A and 3B) from the elongate shape (FIG. 2).

To give more uniform perfusion of medications or therapeutic agents from a deployed stent, a sleeve or coating 32 (FIG. 3B) could be disposed on the exterior of the stent and provided with perforations, cuts or ports to control the dispersion of the medication (by selected location of the perforations, cuts or ports). Alternatively, a liner 36 (FIG. 3B) with perforations, cuts or ports could be provided in the hollow of the wire 4. The sleeve, coating or liner could advantageously be made of urethane or other suitable plastic.

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements.

What is claimed is:

1. A stent configured for disposition in a blood vessel or body duct to maintain the vessel or duct walls apart to maintain patency, said stent comprising an elongate resilient wire having micro-machined cuts formed therein, said wire formed into a helical coil when unconstrained, which can be straightened and inserted lengthwise into and through a catheter for ultimate discharge therefrom to a target location in the blood vessel or duct where the wire resumes a helical coil form configured as a stent to maintain an open profile of the vessel or duct, said cuts being configured to facilitate straightening for delivery through the catheter.

2. A stent as in claim 1 wherein the micro-machined cuts are selectively located on the exterior of the wire to provide flexibility in a direction of greatest curvature of the wire, and stiffness in a direction of least curvature of the wire.

3. A stent as in claim 2 wherein the coil wire includes cuts formed generally transversely of the wire on the inside and outside of the coil.

4. A stent as in claim 3 wherein the coil wire further includes cuts formed generally transversely of the wire on forward sides and rearward sides of the coil.

5. A stent as in claim 4 wherein the coil wire includes more cuts on the inside and outside of the coils than on forward and rearward sides.

6. A stent as in claim 4 wherein the coil wire includes deeper cuts on the inside and outside of the coils than on the forward and rearward sides.

7. A stent as in claim 4 wherein the coil wire includes wider cuts on the inside and outside of the coils than on the forward and rearward sides.

8. A stent as in claim 3 wherein the coil wire is comprised of solid wire.

9. A stent as in claim 3 wherein the coil wire is comprised of tubular wire.

10. A stent as in claim 3 wherein the coil wire is made of nickel-titanium alloy.

11. A stent as in claim 1 wherein the coil wire is comprised of tubular wire for carrying medication in the hollow of the wire, said wire including openings to allow medication carried in the hollow of the wire to flow thereout.

12. A stent as in claim 11 wherein said openings are formed on the outside of the coil.

13. A sent as in claim 11 further including a flexible sleeve disposed over at least a portion of the tubular wire, said sleeve including a plurality of perforations to allow dispersion therethrough of medication carried by the tubular wire.

14. A stent as in claim 11 further including a flexible coating disposed over at least a portion of the tubular wire, said coating including a plurality of perforations to allow dispersion therethrough of medication carried by the tubular wire.

15. A stent as in claim 11 further including a liner disposed in at least a portion of the hollow of the tubular wire, said liner including a plurality of perforations to allow dispersion therethrough of medication carried by the tubular wire.

16. A stent as in claim 13, 14 or 15 wherein the sleeve, coating or liner respectively, are made of polyurethane.

\* \* \* \* \*